(12) United States Patent
McKay

(10) Patent No.: US 6,468,276 B1
(45) Date of Patent: Oct. 22, 2002

(54) SPINAL FIXATION DEVICE AND METHOD

(76) Inventor: Douglas William McKay, 450 Moosa Blvd., Suite C, Eunice, LA (US) 70535

( * ) Notice: Subject to any disclaimer, the term of this patent is extended or adjusted under 35 U.S.C. 154(b) by 0 days.

(21) Appl. No.: 09/393,329

(22) Filed: Sep. 10, 1999

Related U.S. Application Data

(60) Division of application No. 08/767,375, filed on Dec. 16, 1996, now Pat. No. 5,984,922, which is a continuation-in-part of application No. 08/089,788, filed on Jul. 9, 1993, now Pat. No. 5,584,831.

(51) Int. Cl.$^7$ ............................................... A61B 17/56
(52) U.S. Cl. ........................................................ 606/61
(58) Field of Search .............................. 606/61, 60, 72, 606/73, 57, 58, 59, 62, 63, 64–70; 623/17.11; 128/898

(56) References Cited

U.S. PATENT DOCUMENTS

| | | | |
|---|---|---|---|
| 4,794,918 A | * | 1/1989 | Wolter ........................ 606/61 |
| 4,887,595 A | | 12/1989 | Heinig et al. |
| 4,946,458 A | * | 8/1990 | Harms et al. .................. 606/61 |
| 5,030,220 A | | 7/1991 | Howland |
| 5,042,982 A | | 8/1991 | Harms et al. |
| 5,047,029 A | * | 9/1991 | Aebi et al. ..................... 606/61 |
| 5,084,049 A | | 1/1992 | Asher |
| 5,112,332 A | | 5/1992 | Cozad et al. |
| 5,116,334 A | | 5/1992 | Cozad et al. |
| 5,147,359 A | | 9/1992 | Cozad et al. |
| 5,154,718 A | | 10/1992 | Cozad et al. |
| 5,180,393 A | | 1/1993 | Commarmond |
| 5,196,013 A | | 3/1993 | Harms |
| 5,290,288 A | * | 3/1994 | Vignaud et al. .............. 606/61 |
| 5,300,073 A | * | 4/1994 | Ray et al. ..................... 606/61 |
| 5,425,772 A | | 6/1995 | Brantigan |
| 5,458,638 A | | 10/1995 | Kuslich et al. |
| 5,505,732 A | | 4/1996 | Michelson |
| 5,653,761 A | | 8/1997 | Pisharodi |
| 5,658,337 A | | 8/1997 | Kohrs et al. |

FOREIGN PATENT DOCUMENTS

| | | |
|---|---|---|
| EP | 42271 | 12/1981 |
| WO | 9502372 | 1/1995 |

\* cited by examiner

*Primary Examiner*—Henry J. Recla
*Assistant Examiner*—(Jackie) Tan-Uyen T. Ho
(74) *Attorney, Agent, or Firm*—McDermott, Will & Emery

(57) ABSTRACT

A spinal fixation device comprises an intervertebral body wedge which is inserted between vertebral bodies by sequentially expanding the inter-discal space using a spacer. With this sequential expansion, no posterior fixation devices are needed for stabilization of the spinal diseased vertebrae.

17 Claims, 13 Drawing Sheets

SPINAL FIXATION DEVICE AND METHOD

CROSS-REFERENCE TO RELATED APPLICATION

This application is a divisional of application Ser. No. 08/767,375 filed Dec. 16, 1996, U.S. Pat. No. 5,984,922, which is a continuation-in-part of application Ser. No. 08/089,788, U.S. Pat. No. 5,584,831, entitled SPINAL FIXATION DEVICE AND METHOD, filed Jul. 9, 1993.

BACKGROUND OF THE INVENTION

This invention relates to an apparatus for spinal column fixation. More particularly, but not by way of limitation, this invention relates to a mechanical device used to obtain a rigid posterior spinal column fixation in order to obtain a rigid posterior spinal column bony fusion for disabling back and leg pain.

In one embodiment, the apparatus includes a posterior fixation device which is attached to the involved vertebral bodies. The attachment is made by pedicle screws penetrating into the vertebral body with rigid attachment to ball-and-socket clamps and rods.

The invention also may include a pair of intervertebral metallic or radiolucent wedges inserted into the disc space of the involved vertebrae to increase the stability of the spinal column anteriorly and to avoid breakage of the pedicle screw. Additionally, the application also discloses a method of placing the fixation and wedge device in a posterior lateral approach.

Posterior spinal fusions have been performed on millions of people since at least the early 1900's. The principle of bony fusion has been and still is stabilization or prevention of motion between two adjacent vertebral bodies.

The most recent attempt to stop motion of the spinal column in order to obtain spinal fusion is internal fixation. One design consist of a series of hooks, rods, screws and wires attached to the lamina or spinous processes to correct deformity or to stabilize the spine.

Another design utilizes screws inserted posteriorly through the pedicle into the vertebral body connecting to plates, rods and clamps to stabilize the two adjacent segments.

The prior art pedicle screw devices have different functions. One function includes the correction of the degenerative curve of the lumbar spine between L3 and S1 or traumatic deformities. These devices have the internal purpose of this device is correction of a deformity through two vertebra such as seen in U.S. Pat. No. 4,987,892 to Martin H. Krag, and in U.S. Pat. No. 5,047,029 to Max Aebi and Robert Mathys, Jr.

Another function includes rigidly fixing the spinal column using a combination of intra-vertebral screws, plates, rods and clamps. In general, see U.S. Pat. Nos. 4,615,681, 4,648,388, 4,655,199 to Steffie; 4,754,326, to Burton; 4,950, 269 to Gaines; 4,653,481 to Howland; 4,913,134 to Luque; 4,836,196 to Parke and Weinstein; 4,946,458 to Harms; 5,030,220 to Howland; 4,887,595 to Heinig; and 5,042,982 to Harms.

Another function includes flexible or semi-rigid fixation shown in U.S. Pat. Nos. 4,913,134 to Luque; and, 4,743,260 to Buttem.

The present invention utilizes the rigid posterior fixation device which is attached to the involved vertebral bodies through pedicle screws connected with a series of operably associated ball-and-socket clamps and rods. One such device using a ball connector is seen in U.S. Pat. No. 4,946,458 to Harms. However, the prior art devices include several disadvantages. For instance, many devices were susceptible to breakage, and once breakage occurs, the devices are very difficult to retrieve. Also, the mechanism of clamps and rods is very complicated and difficult for the surgeon to install.

Furthermore, in both the rigid and flexible type of devices, the pedicle screw developed excessive motion and toggle. This in turn would cause the plate to become loose thereby allowing the plate to slide back and forth causing irritation, lack of fixation, and thus failure of fusion.

The rigid devices without inter-body fusion or rigid spacer will result in breakage in the screw because of mechanical factors. The greatest portion of the weight of the individual is taken through the vertebral body and disc. The center of motion of the vertebral segments is located in the posterior aspect of the disc. In the lower lumbar spine the greatest amount of motion is flexion and extension of the trunk, therefore, the intervertebral segment motion is mainly to the anterior frontal or posterior backward movement. Rigid posterior fixation is at a mechanical disadvantage because the forces of weight and motion are anterior to the rigid posterior fixation device. With repetitive motion the device either breaks or becomes loosened. With loosening or breakage, the motion will increase leading to more pain and failure.

Sciatica is pain which shoots down the posterior lateral aspect of the leg. Sciatica is caused by impingement or encroachment on the neural elements in the lumbar spine. Recent studies indicate that intervertebral body fusion is the most effective relief of sciatica. This is because the intervertebral disc is the mechanical center of motion between the intervertebral bodies, and the majority of the body weight of the individual is taken through the vertebral bodies.

Prior art devices are designed and placed in the intervertebral disc comprise several concepts. One is to replace the disc which has been removed with an artificial disc material which can function and behave biomechanically similar to the normal intervertebral disc when inserted in the space.

A second includes maintaining the disc height with no attempt at inter-body fusion. A spacer is placed in after removal of the intervertebral disc.

A third involves maintaining height and obtaining a fusion with a fenestrated spacer that will contain a bone graft. The fenestrated spacer is placed in directly posteriorly under the neural elements.

This invention solves these problem by combining the wedge insert anteriorly and the rigid posterior fixation device allowing the patient to obtain a solid, rigid fixation. The purpose of the wedge is to obtain anterior stabilization, restoration of intervertebral disc height, normal physiological lumbar lordosis, and intervertebral body bony fusion in the human spinal column. The posterior device stabilizes the mechanical dynamics associated with posterior forces, and the wedge compensates the forces associated with the anterior forces.

SUMMARY OF THE INVENTION

The invention includes both apparatus and method claims to a spinal column fixation device that includes multiple clamping means for clamping onto an implanted screw in the sacrum and involved vertebrae of a patient. The clamping means will also contain a stabilizing rod and a portion to receive a receptacle stabilizing rod from a complementary clamping means.

In one embodiment, the invention comprises a first sacrum clamping means for clamping to an implanted first sacrum screw in the pedicle of the person's sacrum, said first sacrum clamping means containing a stabilizing rod. The apparatus will also contain a second sacrum clamping means for clamping to an implanted second sacrum screw in the pedicle of the person's sacrum, the second sacrum clamping means containing a stabilizing rod.

The invention will contain a first vertebrae clamping means for clamping to an implanted first vertebrae screw in the pedicle of an involved vertebrae, with the first vertebrae clamping means receiving the stabilizing rod of said first sacrum clamping means. A second vertebrae clamping means for clamping to an implanted second vertebrae screw in the pedicle of an involved vertebrae is also provided, with the second vertebrae clamping means receiving the stabilizing rod of the second sacrum clamping means.

In one embodiment, the first vertebrae clamping means further contains a stabilizing rod, and wherein said second vertebrae clamping means contains a stabilizing rod, and the apparatus further comprises a third vertebrae clamping means for clamping to an implanted third vertebrae screw in the pedicle of an involved vertebrae, with the third vertebrae clamping means receiving said stabilizing rods of said third securing means. Also, a fourth vertebrae clamping means for clamping to an implanted fourth vertebrae screw in the pedicle of an involved vertebrae is furnished, with the fourth vertebrae clamping means receiving the stabilizing rods of said second vertebrae clamping means.

In one embodiment, the fourth vertebrae clamping means further contains a stabilizing rod, and the apparatus further comprises a first interconnecting means for interconnecting the stabilizing rod of the fourth and second clamping means. The third vertebrae clamping means contains a receiving portion, and the apparatus further contains a second interconnecting means for interconnecting the stabilizing rod of the first and third clamping means.

The implanted screws contain a first end and a second end, and wherein said first end contains external thread means for threading the implanted screws into the spinal column of the person, and more particularly into the pedicle of the involved vertebra, and sacrum. The second end contains a multi-sided, generally a hexagon, shaped nut member. Further, the hexagon shaped nut member has attached thereto a spherical handle end.

The first, second, third and fourth sacrum, as well as the first, second, and fifth vertebrae clamping means comprises a cap portion having an aperture therein, and wherein the cap portion has a first and second cavity formed therein, the first cavity being formed for receiving the spherical handle ends of the pedicle screws and the second cavity being formed for receiving the stabilizing rods. Also included is a base portion having an aperture therein, and wherein said base portion has a first and second cavity formed therein, the first cavity being formed for receiving the spherical handle ends of the pedicle screws and the second cavity being formed for receiving said stabilizing rod. Next, a bolting member fitted through the aperture of the base and the cap is included and cooperating with the base and the cap so that the spherical handle end and stabilizing rods are adapted to be received within the mating cavities.

The stabilizing rod may extend from the third and fourth sacrum clamping means and has a spherical handle end, and the third vertebrae and fourth vertebrae clamping means will comprise a cap portion having an aperture therein, and wherein the cap portion has a first and second cavity formed therein, the first cavity being to receive said spherical handle end of the pedicle screws and the second cavity being formed for receiving the spherical end of the stabilizing rod, a base portion having an aperture therein, and wherein the base portion has a first and second cavity formed therein, with the first cavity receiving the spherical handle end of the pedicle screws and the second cavity being formed for receiving the spherical end of the stabilizing rod. Also included will be a bolting member fitted through the aperture of the cap and base, and cooperating with said cap and base so that the spherical handle end of the implanted screw and stabilizing rod are adapted to be received within the mating cavities.

In the preferred embodiment, the apparatus may further comprise an intra-vertebral body wedge. The wedge will contain a first end having a tapered end increasing in size; a second end having a tapered end increasing in size; and wherein the first end taper and the second end taper converge at a point which forms the greatest width of the wedge. The wedge member will contain an opening therein for placement of a bone so that a bone graft may be performed. Further, the wedge may contain a threaded aperture for placement of bolting means for placement of an inserter to secure the wedge member for insertion into the discal space in a sagittal plane.

The application also discloses a method of stabilizing motion of involved spinal diseased vertebrae with a spinal fixation device, the spinal fixation device containing a plurality of implanted screws, the implanted screws containing a first and second end, the first end containing thread means and the second end containing a spherical handle end, the spinal fixation device further containing a plurality of spherical clamp means for securing onto the spherical handle ends. The device also contains a plurality of interconnecting rods for interconnecting the ball clamp means. Finally, a wedge member is provided for insertion into inter-discal space.

Generally, the method comprises the steps of performing two posterior lateral incisions or alternatively, one posterior incision on the back of the patient to the area of the involved spinal diseased segments.

Next, the method will expose the transverse process (FIG. 19, 224) of the involved spinal diseased segments; then, dissecting between and lateral to the transverse process of the involved spinal diseased vertebrae is performed so that the nerve roots (FIG. 19, 216) and the annulus fibrosis (FIG. 18, 210) are exposed. Subsequently, a cruciate incision is placed in the annulus fibrosis (FIG. 18, 210) posterior laterally near the intervertebral foramen; then, the surgeon removes the gelatinous disc material and cartilage end plate of the involved spinal diseased vertebrae.

The surgeon then determines the proper size and length of the intra-pedicle screws and the drill point of the drill is placed on the vertebral body at the pedicle starting at the base of the transverse process. A bore hole is then drilled in the pedicle of the involved spinal diseased vertebrae or sacrum for placement of the pedicle screw. The pedicle screw is then rotated into the bored openings of the involved spinal diseased vertebrae with the wrench; and, the surgeon applies a spreader to the pedicle screws so that the disc is opened for placement of the wedge member.

The method may also include the steps of selecting the proper length, height, angle of the wedge member, and then placing a bone in small pieces into the inter-discal space of the involved spinal diseased segments, and in the fenestration of the wedge for intervertebral fusion prior to insertion of the wedge 180. In selecting the proper wedge member, a test wedge may be first employed on a trial basis in order to instre selection of the correct size, length and angle of the wedge.

Following this step, the wedge is inserted (FIGS. 16 and 17A–E) into the inter discal space of the involved spinal diseased vertebrae bilaterally, and the spreader is released which had been keeping the intra-pedicle screws separated thereby allowing the elasticity of the annulus fibrosis and adjacent tissue to lock the wedge in inter-discal space.

Subsequent to this step, the position of the intra-pedicle screws is examined with an image intensifier, and the ball clamp means is placed about the spherical handles of the implanted screws. The fastener member (nut) is tightened so that the ball clamp means will not slip off the spherical handle of the implanted screw. The surgeon will then determine the particular structural arrangement of the interconnecting stabilizing rods.

Next, the cutting of the interconnecting stabilizing rods is performed, with or without spherical balls on the end, to the proper length, and the interconnecting rods are placed into the ball clamp means so that the ball clamp means are linked; and tightening of the ball clamp means is executed so that the ball clamp means encases the spherical handle end and the interconnecting rods. Because of the curved contour of the spinal column, some bending and shaping of the rods may be necessary.

The application also includes a step wherein the process of placing the drill point on the involved spinal diseased vertebral bodies and drilling a bore hole in the ienvolved spinal diseased vertebral bodies includes: placing the drill point on a first and second site of the pedicle of the sacrum; then, placing the drill point on a first and second site of the ala of the sacrum and drilling a bore hole to the first and second site on the ala of the sacrum; then, placing the drill point on a first and second site of the pedicle of the L5 involved spinal diseased vertebral body and drilling a bore hole to the first and second site of the L5 involved spinal diseased vertebral body; and, placing the drill point on a first and second site of the pedicle of the second involved spinal diseased vertebral body and drilling a bore hole to the first and second site of the L4 involved spinal diseased vertebral body.

At this point, completion of the application of the posterior intra-pedicle spinal fixation device is completed. The particular structure arrangement will vary on a case-by-case basis. Thus, the figures of this application show one possible sequence; however, other arrangements will depend on the particular circumstances so that the connections and cross connections can be many different arrangements.

A feature of the present invention includes the ability of using one or two screws on each side of the sacrum. Another feature includes use of triangular cross fixation rods to increase posterior stability. Yet another feature is that when combined with the wedge of the present invention, the device increases stability of the spinal column anteriorly and to avoid breakage of the implanted screws, the wedge creates support in the inter-discal space as well as creating the normal lordosis and increasing stability.

Another feature includes fewer moving parts which allows for the clamps to be mechanically cross connected. Another feature consist of the ball in the socket concept which allows for connecting two clamps at variable angles in both a horizontal and vertical plane, depending on the circumstances of each individual patient. The interconnecting stabilizing rods with a spherical handle end can rotate while in place in the clamping means up and down, as well as laterally relative to the implanted screw.

Still another feature includes the capability of measuring the length of the stabilizing rods during the procedure and cutting the rods to the appropriate length in order to conform to the particular circumstances of the patient. Still yet another feature consist of having less fiddle factor. Another feature consist of having the stem as the weakest point of the implanted screw member which allows for easy removal of the screw if breakage occurs. Put another way, the screw can easily be extracted because the nut and the penetrated portion of the screw is still intact.

An advantage of the present invention includes that the device is easy to insert. Another advantage is that the device allows for adjustable tightness of the various securing means. Yet another advantage includes avoiding breakage of screws.

Another advantage is that multiple clamps connecting to individually associated intra-pedicle screws allows for variations in the number of connecting rods and the variations in the pattern of interconnection. Still another advantage includes that the lamina and the spinous process are not disturbed which leaves a large area for bone grafting. Yet another advantage of the procedure allows for ease of facet joint fusion.

Still another advantage consist of the anterior and the posterior rigid fixation and the large bone grafting area achieved by this invention which leads to solid bony fusion.

Another aspect of the invention involves use of the intervertebral wedge alone for spinal column fixation. The wedge is inserted by expanding the inter-discal space between two vertebrae until a maximum inter-discal space is reached. The implant is inserted between the two vertebrae and is press fit therein. With this press fit, there is no need to use the clamping means and implanted screws described above. To facilitate insertion of the wedge, the facet joint is excised to open the vertebral foramen.

The wedge can include a rounded head to facilitate insertion and serrated side edges to prevent posterior extrusion. The wedge body can be solid for individuals requiring more structural surface for support. The spacers used to press fit the wedges can also have rounded leading edges.

BRIEF DESCRIPTION OF THE DRAWINGS

FIGS. 22A, 22B, and 21C illustrate the compressor device.

DESCRIPTION OF THE PREFERRED EMBODIMENTS

Figure 1:
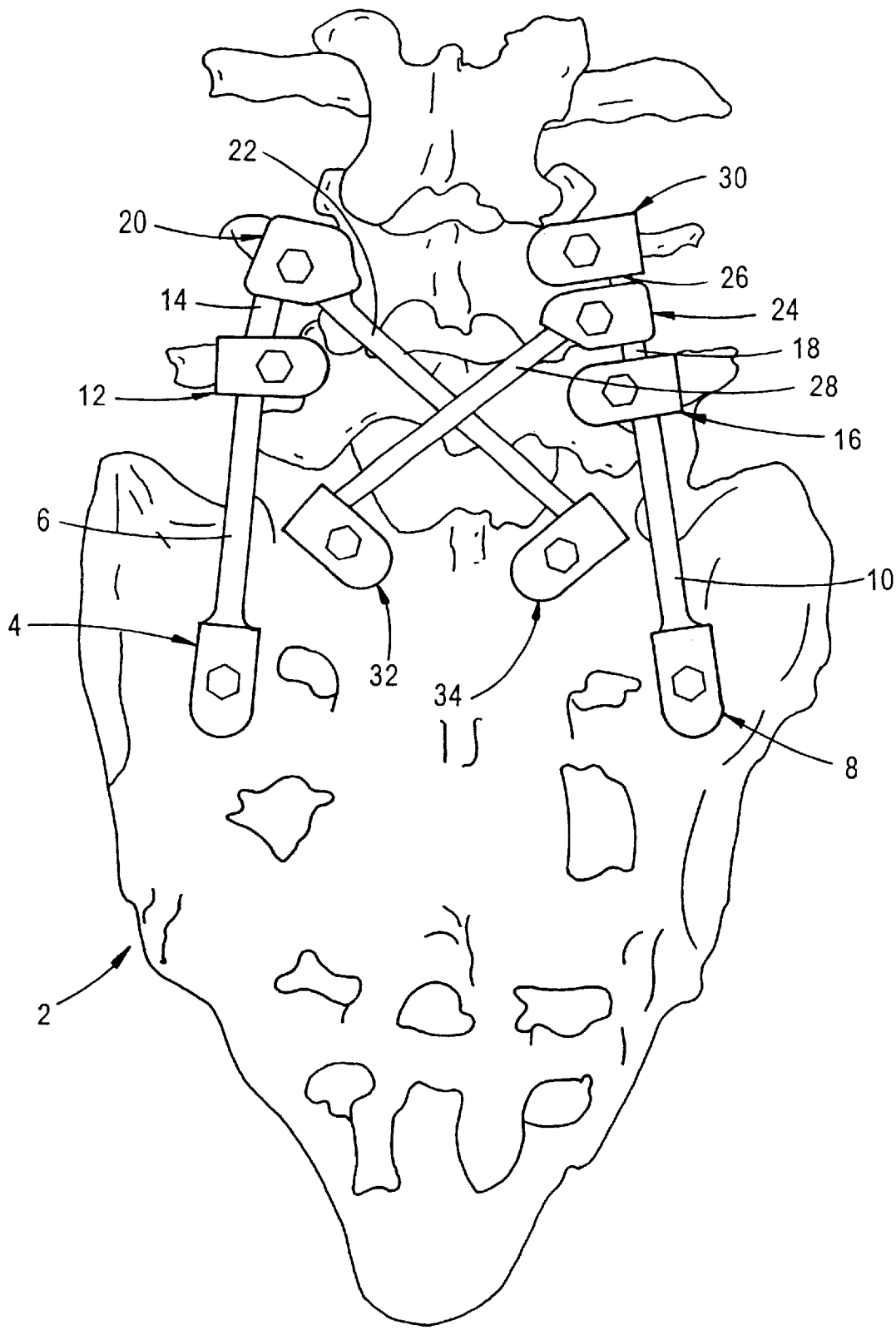
FIG. 1 is an illustration of the spinal column bony elements viewed from the posterior of the human.

Like numbers in the various figures refer to like components throughout the application. Referring to FIG. 1, the spinal column bony elements are depicted. Generally, the sacrum 2 is shown that will have the first sacrum clamping means 4 for clamping to an implanted first sacrum pedicle screw in the alae of the sacrum 2. The pedicle screw will be described in greater detail later in the application. It should also be noted that the sequence of interconnection of the various clamping means may be adjusted on a case-by-case basis, and as such, FIG. 1 depicts one possible arrangement. Other arrangements of the clamping means are possible.

First stabilizing rod 6 will extend from the clamping means 4. A second sacrum clamping means 8 for clamping to an implanted second sacrum screw to the opposite side, in the alae, of the sacrum may also be provided. The clamping means 8 will have second stabilizing rod 10 extending therefrom.

A first vertebrae clamping means 12 for clamping to an implanted first vertebrae screw to the involved vertebra, which in FIG. 1 is the fifth lumbar vertebra, may also be provided. The first vertebrae clamping means will have connected thereto first stabilizing rod 6, as well as having third stabilizing rod 14 extending therefrom.

A second vertebrae clamping means 16 will be attached to the involved vertebra by means of an implanted second vertebrae screw, which in FIG. 1 is the fifth lumbar vertebra. The second vertebrae clamping means 16 will have connected thereto second stabilizing rod 10, as well as having fourth stabilizing rod 18 extending therefrom.

A third vertebrae clamping means 20 is used for clamping to an implanted third vertebrae screw in the pedicle of an involved vertebra, which in FIG. 1 is the fourth lumbar vertebra. The clamping means 20 will have connected thereto third stabilizing rod 14, as well as having first cross stabilizing rod 22 extending therefrom. It should be noted that other vertebrae clamping means (not shown) for clamping to other implanted vertebrae screws in the pedicle of other involved vertebrae may be provided as deemed necessary by the surgeon. The various clamping means will be interconnected by stabilizing rods.

A first interconnecting (or cross-connecting) means 24 for interconnecting the stabilizing rods from second clamping means 16 may also be provided. The first interconnecting means 24 will have connected thereto fourth stabilizing rod 18, as well as having fifth stabilizing rod 26 and second cross stabilizing rod 28 extending therefrom.

The invention will also contain a fourth vertebrae clamping means 30 for clamping to an implanted fourth pedicle screw (not shown). Fourth clamping means 30 will be cross attached with the first interconnecting means 24 by means of first stabilizing rod 26. This structural connection aids in balancing the distribution of stabilizing forces. Alternatively, fourth clamping means 30 may be connected directly to fifth stabilizing rod 26. A second interconnecting means could be used between first vertebrae clamping means 12 and third vertebrae clamping means 20.

A third and fourth sacrum clamping means 32, 34 for clamping to an implanted third and fourth sacrum alae screw to the sacrum 2 may also be included. The clamping means 32, 34 will be cross attached with the clamping means 20, 24 by means of first cross stabilizing rods 28 and second cross stabilizing rod 22. This cross structural connection aids in balancing the distribution of stabilizing forces.

Figure 2:
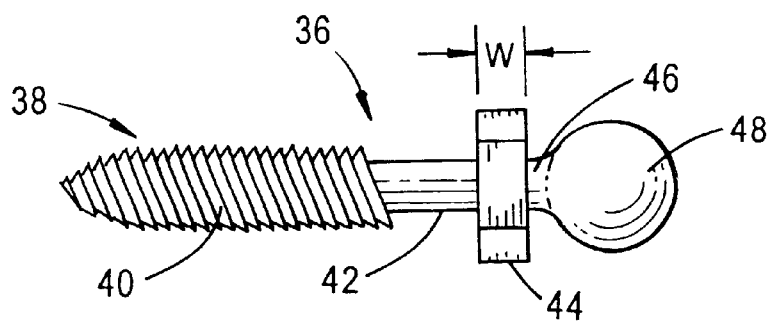
FIG. 2 is a cross-sectional view of the intra-pedicle screw.

Referring now to FIG. 2, the screw 36, used in the pedicle of the involved vertebra, sacrum as well as the ala of the sacrum, will now be described. It should be noted that through out the application, the terms screw and intrapedicle screw will be used interchangeably. The screw 36 will have a first end 38 that will have contained thereon external thread means 40 for boring into the involved sacrum and vertebra. The thread means will be of standard course thread for cancellus bone.

The thread means 40 extend to the smooth cylindrical surface 42, that in turn extends to the multi-sided (usually six) nut member 44, which may vary from 3 to 6 millimeters in width w. The nut member 44 will then conclude at the stem 46. In the preferred embodiment, the stem 46 will have the smallest outer diameter of the intra-pedicle screw 36 so that the stem will be the weakest point of the screw 36, and therefore, the stem will be the first to break. Also, the stem 46 increases the distance from the clamp to the bone for ease of bone grafting.

The stem 46 extends to the second end 48 which in the preferred embodiment will be excoriated on its surface and the actual size of the ball portion will vary between 6 and 12 millimeters.

Figure 3A:
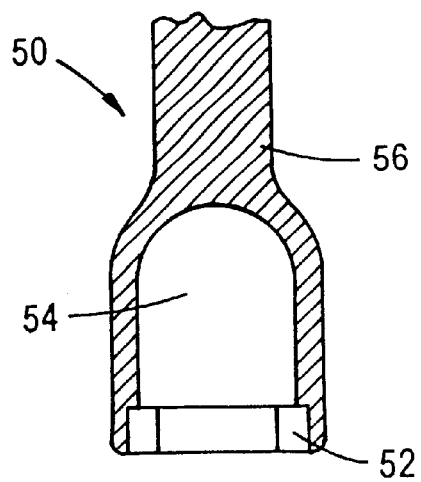
FIG. 3A is a cross-sectional view of the wrench of the present invention.
Figure 3B:
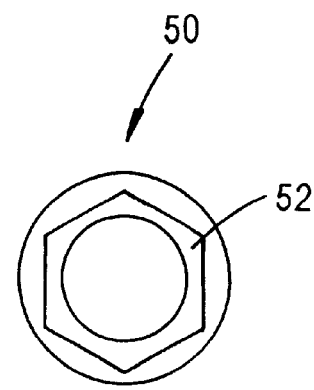
FIG. 3B is a bottom view of the wrench seen in FIG. 3A.

Referring to FIG. 3A, the wrench 50 of the present invention is illustrated. The wrench 50 will generally comprise a receiving segment 52 that will reciprocally receive the hexagon nut member 44. The wrench 50 will also contain a cavity 54 that is a recess for receiving the spherical handle end 48. The actual wrench handle means 56 for allowing the surgeon to fasten the nut member 44 will be connected to the receiving segment 52. FIG. 3B depicts the bottom view of the wrench 50.

Figure 4A:
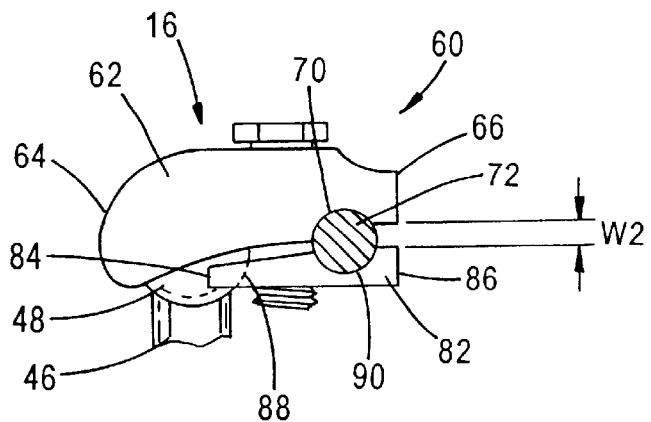
FIG. 4A is an illustration of the main connector clamp of the invention secured to the ball of the intra-pedicle screw.

Turning now to FIG. 4A, a typical main connector clamp depicted as the vertebrae clamping means 16, which also is seen in the vertebrae clamping means 30, is shown and will be explained in greater detail. The main connector clamp will have cap member 62 that will have a first end 64 and a second end 66, and wherein the first end 64 has a generally spherical configuration that forms a cavity 68, as better seen in FIG. 4B, that receives the spherical handle end 48.

The second end 66 of the main connector clamp 16 will contain a second cavity 70 that is shaped so as to receive a stabilizing rod 72. The stabilizing rods of this invention can be round, as shown, square or some other configuration. The stabilizing rods may be manufactured out of stainless steel, titanium, or plastic. The cap member 62 will also contain an aperture 74, as better seen in FIG. 4B, that will receive a bolting member 76, that may have a hexagon nut head 78 and a threaded end portion 80.

Figure 4B:
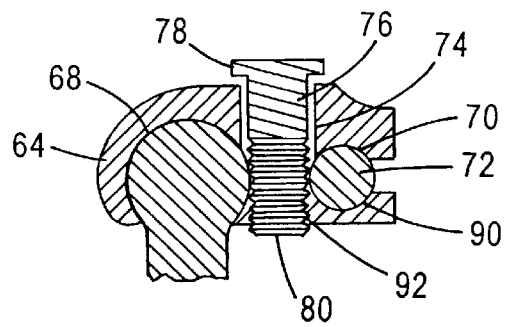
FIG. 4B is a cross-sectional view of the main connector clamp seen in FIG. 4A.

The base member 82 will have a first end 84 and a second end 86, with the first end 84 having a cavity 88 that will have fitted therein a segment of the spherical handle end 48. The second end will also have a cavity 90 that will have a segment of the stabilizing rod 72 fitted therein, as well as an aperture 92 that will have the bolting member 76 fitted therein, as seen in FIG. 4B. The bolting member 76, cap member 62 and base member 82 cooperate with one another so that the spherical handle end 48 and stabilizing rods are adapted to be received within the matting cavities 68, 88 and 70, 90 and secured together as the bolting member 76, 80 threadedly attaches the cap member and base together (which can also be seen in FIG. 8). A lock washer, though not shown, may also be employed in order to lock the bolting member in place.

The main connector clamp 16 may have the cap member 62 and base member 82 manufactured generally from steel, but titanium, and/or plastic can also be used.

Figure 5:
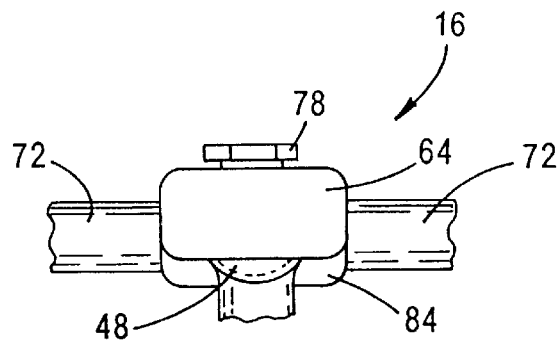
FIG. 5 is a front view of the main connector clamp.

Referring now to FIG. 5, the front view of the main clamp 16 is depicted. This view depicts the first end 64 of the cap member 62 and the base member 82 engaged with the spherical handle end 48 of the pedicle screw 36, as well as the stabilizing rod 72 which exits from both sides of the main connector clamp 60.

Figure 6:
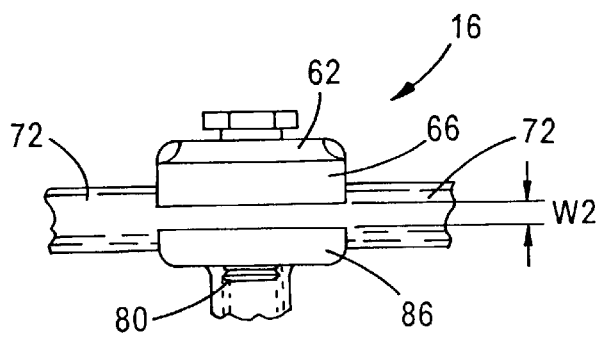
FIG. 6 is a rear view of the main connector clamp.

Turning to FIG. 6, the rear view of the main connector clamp 16 is illustrated. This view shows the second end 66 of the cap member 62, as well as the second end 86 of the base member 82, with the threaded end 80 of the bolting member 76. It should be noted that the void (width) W2 is in place after securing the base 82 and cap member 62 together to ease placing the rod 72 in the cavities without difficulties.

Figure 7:
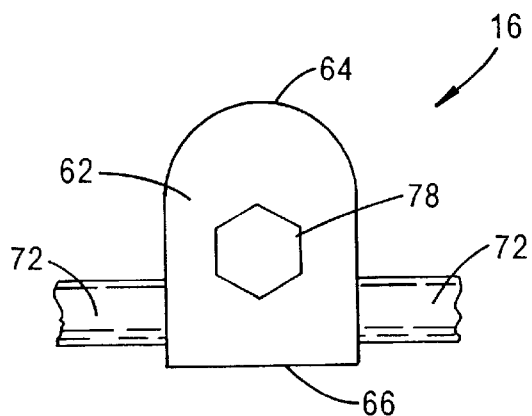
FIG. 7 is a top view of the main connector clamp as seen from the posterior during application.

Turning now to FIG. 7, the top view of the main connector clamp 16, as seen from posterior during application, is illustrated. This figure shows the stabilizing rods 72 operatively attached to the main connector clamp 60. Also, the first end of the cap member 64 is shown, as well as the second end of the cap member 66. Also, the hex nut head 78 is shown.

Figure 8:
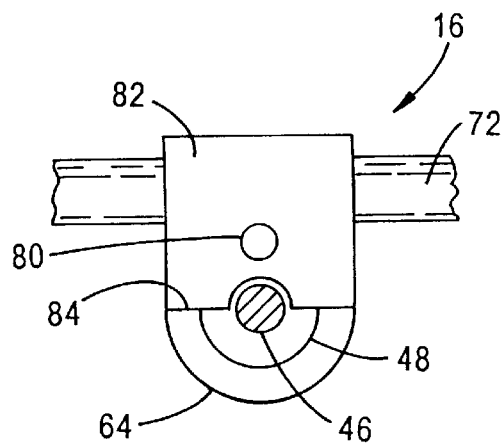
FIG. 8 is a bottom view of the main connector clamp.

In FIG. 8, the bottom view of the main connector clamp 16 is illustrated. In this figure, the stabilizing rod 72 is shown, as well as the second end 86 of the base portion 82. A cross-section of the intra-pedicle screw stem 46.

The first end of the plate 84 surrounds half of the spherical handle 48 with a recess around the stem. Thus, because of the contour of the cavity 88 which surrounds the perimeter of the spherical handle 48, when the hex head nut 78 is tightened, the threaded portion 80 will lock the base member and cap portion together and beginning moving the base member 82 and cap 62 together, which in turn effectively clamps the spherical handle end 48 and stabilizing rod 72 in the respective cavities of the base member 82 and cap member 62. The cavities can be excoriated in order to more easily obtain the proper amount of friction between the cavities and the stabilizing rod 72 and/or spherical handle 48.

Figure 9:
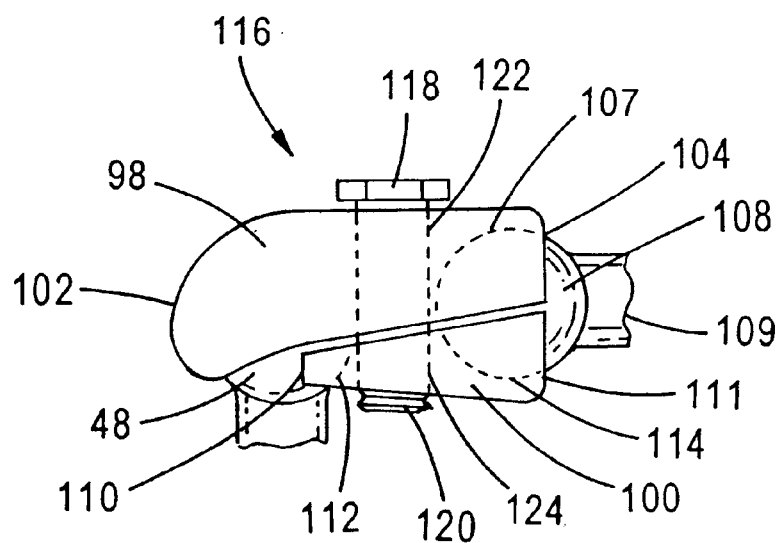
FIG. 9 is an illustration of a modified main connector clamp secured to the ball of the intra-pedicle screw as well as the ball of the connecting rod.

Referring to FIG. 9, a modified main connecting clamp 4, which in FIG. 1 is the first sacrum clamping means, is illustrated. The modified clamp 4 will have a cap member 98 and a base portion 100. The cap member 98 will have a first end 102 and a second end 104. The first end will be of general spherical construction and contain an inner cavity 106 (not shown) that is adapted to receive the spherical handle end 48 of the intra-pedicle screw 36. A second cavity 107 is also provided to receive the spherical end 108 of a stabilizing rod 109.

The base member on 100 will also contain a first end 110 and a second end 111 that will have first cavity 112 that will receive the bottom portion of spherical handle end 48. A second cavity 114 is also formed thereon, which will receive the spherical end of a stabilizing rod. The modified clamp 4 connects the ball of the intra-pedicle screw to the connecting rod which in this case has a ball, or spherical handle end. The modified clamp 96 is best utilized in the sacrum as seen in FIG. 1, securing means 4 and 8, but also can be used on the upper vertebral connections if deemed appropriate by the surgeon.

The cap member 98 and base member 100 will be secured together by means of the bolting member 116, with the bolting member containing a hexagon head 118 similar to the hex head nut 78. The bolt member 116 will also contain thread means 120. The cap member 98 and base member 100 will contain apertures 122 and 124 respectfully, that will receive the bolt, and aperture 124 will contain internal thread means that will cooperate with the thread means 120 so that as the bolt 116 is threaded into the aperture 124, the base member 100 and cap member 98 will be joined together and will lock the spherical handles 48 and 108. When the hexagon head 118 is tightened, the two halves cover approximately two-thirds of the diameter of the ball 108 of the connecting rod 109 which in the preferred embodiment is excoriated and locks the ball 108 rigidly.

Figure 10:
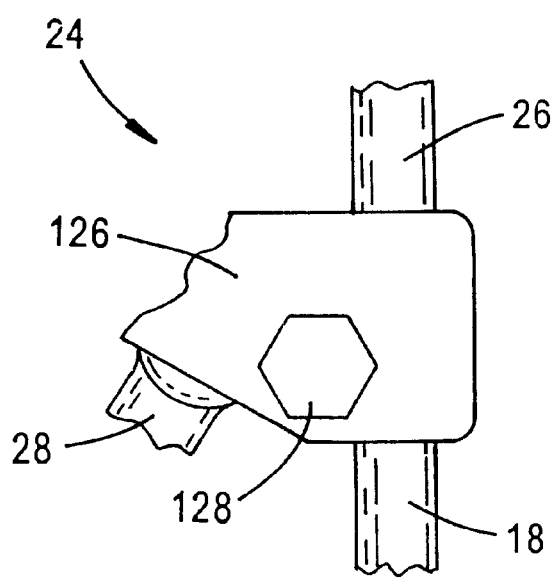
FIG. 10 is an illustration of another modified main connector clamp when the invention requires three units connected to one clamp.

Referring now to FIG. 10, an interconnecting type of main connector 24, such as the first interconnecting means 24 of FIG. 1, is shown. This type of inter-connector may be utilized when the system of connectors chosen by the surgeon requires three clamp means connected at a particular location. The inter-connector 24 will have the stabilizing rods 18 and 26 connected thereto. Also, the cross-stabilizing rod 28 will be connected, with the spherical handle end 48 being disposed within the connector 24. The spherical handle 48 and stabilizing rods 18 and 26 will be disposed within the connector 24 by means of the cap portion 126 and the base portion (not shown) being fastened together by the bolting member 128, as previously described.

Figure 11:
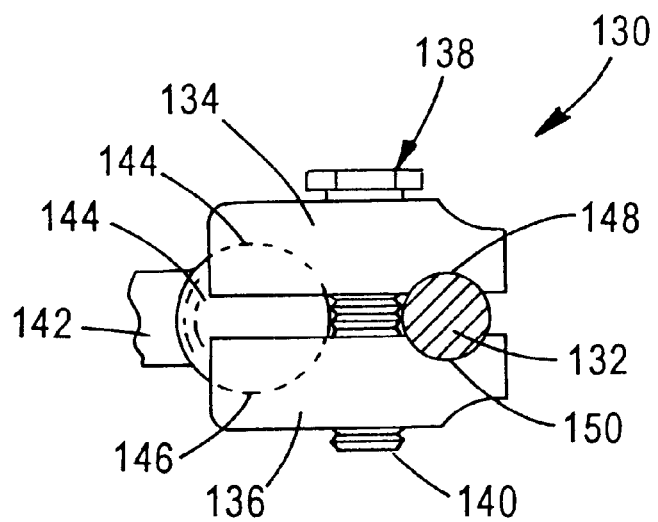
FIG. 11 is an illustration of a cross connecting clamp.

FIG. 11 depicts another cross connecting clamp 130 that is not necessarily shown in FIG. 1. The cross connecting clamp 130 is utilized to connect a connecting rod to a cross connecting rod. The cross connecting clamp 130 can be at 90 degrees from one cross connecting rod to the other. While only the 90 degree situation has been shown, other clamps can be at angles that range from 0 to 90 degrees, with the angles shown in FIG. 1 being 30 degrees and 45 degrees.

In FIG. 11, the stabilizing rod 132 is inserted between the cap member 134 and the base member 136. A bolting member 138, with lock washer 139 and thread means 140, is provided in order to fasten the cap 134 and base member 136 together as previously described.

Figure 12:
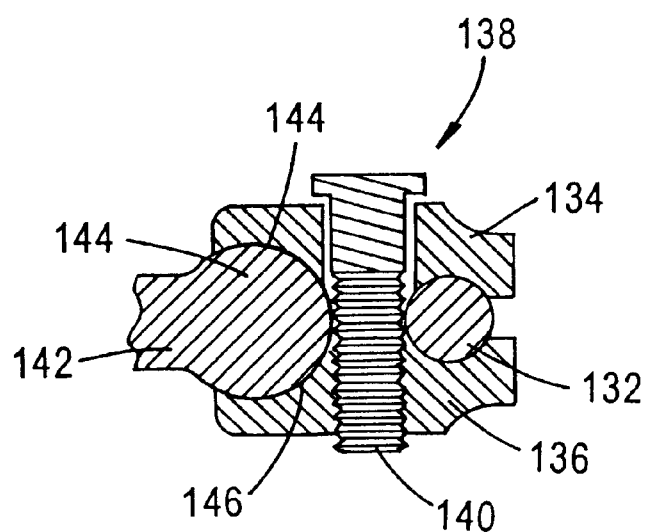
FIG. 12 is a cross-sectional view of the cross connecting clamp of FIG. 11.

A connecting, or stabilizing, rod 142 with the attached spherical end 144 having been encircled within a first cavity 144 located within the cap, member 134 and a second cavity 146 located within the base member 136, as depicted in FIG. 12 which is a cross-sectional view of FIG. 11. It should be noted that other rods may have attached thereto, if desired, a spherical end similar to that shown in FIGS. 11, 12. The cap will also have a cavity 148 for placement of the stabilizing rod 132, as well as mating cavity 150.

In the embodiment shown in FIGS. 11 and 12, when the cap member 134 and base member 136 are tightened, the cap member 134 and base member 136 will generally cover two-thirds of the diameter of the ball, and with the tightening of the bolting member 138, the clamp becomes as rigid as preferred by the surgeon. Due to the posterior application of these devices, the bolting member 138 is tightened from the back of the patient (i.e. the spinal column) which makes for easy application.

Figure 13:
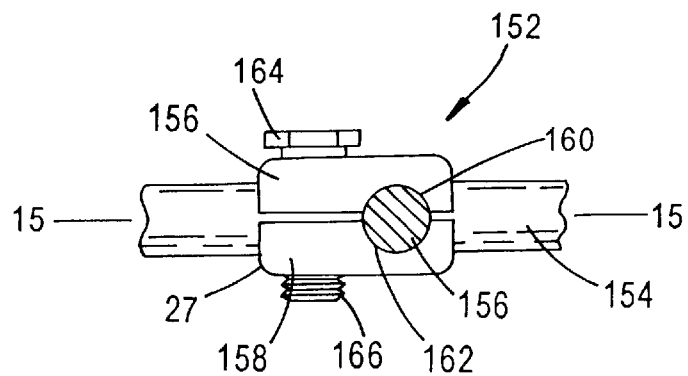
FIG. 13 is an illustration of a modified cross connecting clamp.

FIG. 13 is another alternate cross-connecting clamp 152 which can be used to connect a connecting rod 154 to a second connecting rod 156. Like the other clamps previously discussed, the clamp 152 will have a cap member 156 and a base member 158, with the cap member 156 having a first cavity (not shown) for placement of the rod 154, and a second cavity 160 for placement of the rod 156. The base member 158 will likewise contain a cavity (not shown) for placement of the rod 154, and a second cavity 162 for placement of the rod 156.

Figure 14:
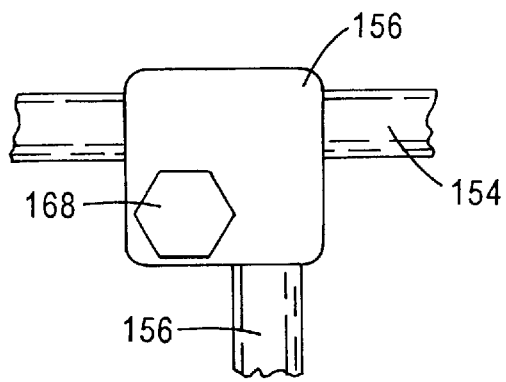
FIG. 14 is an illustration of another modified cross connecting clamp.

The bolting member 164 with lock washer (not shown) will be placed through apertures in the cap member 156 and base portions 158, with the member 164 having thread means 166. The bolting member 164 will have hexagon head 168, as seen in FIG. 14. The cap member 156 and base member 158 will be attached to one another by means of the bolting member 164 as previously described which will effectively lock the rods 154 and 156 in place.

Figure 15:
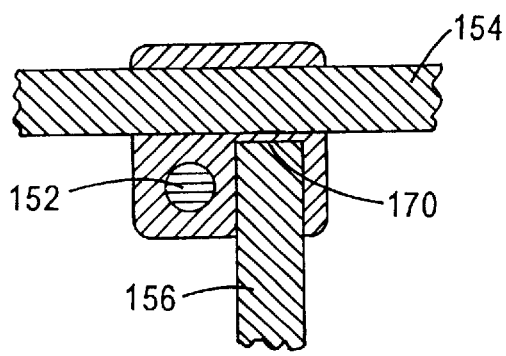
FIG. 15 is a cross-sectional view of the modified cross connecting clamp of FIG. 14.

Turning now to FIG. 15, a cross-sectional view of the alternate cross-connecting clamp 152 taken along line 15—15 of FIG. 13 is illustrated. As shown, the rod 154 is continuous therethrough; however, the rod 156 terminates at rod end 170. It should be noted that the embodiments depicted in FIGS. 13–15 can be made at 90 degrees as illustrated from one connecting rod to the other or it can be at 45 or 30 degrees, depending on the circumstances and the discretion of the surgeon.

Figure 16:
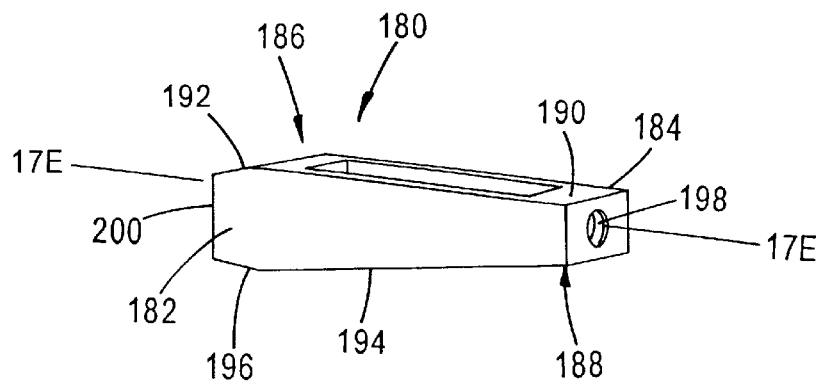
FIG. 16 is a three dimensional illustration of the intravertebral wedge.

With reference to FIG. 16, a three dimensional view of the intervertebral body wedge 180 is shown. The wedge 180 is generally a rectangular shaped device made from either stainless steel, titanium, fiberglass, or other suitable material. The height of the device can vary from 6 to 16 millimeters. The width of the device can vary from 8 to 16 millimeters. The device is wedged shaped with varying degrees of taper, from 4 to 20 degrees. All of these various measurements may vary, depending on the needs of the intra-vertebral space.

The wedge 180 will comprise a first side 182, second side 184, a top side 186, and a bottom side 188. The top side 186 contains a first angled surface 190 that concludes at second angled surface 192. The bottom side 188 will contain a first angled surface 194 that terminates at the second angled surface 196. The angled surfaces of the top 186 and bottom 188 sides provides for a wedged device. The wedge 180 also contains a first end 198 and a second end 200.

Figure 17E:
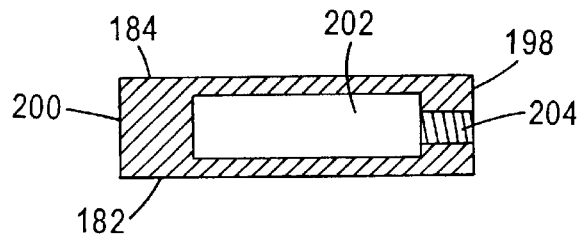
FIG. 17E is a cross-sectional view of the wedge seen in FIG. 16.
Figure 17A:
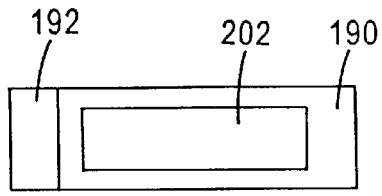
FIG. 17A is an illustration of the top of the wedge seen in FIG. 16.

FIGS. 17A–17E depicts various views of the wedge 180 which will now be discussed. FIG. 17A is a top view of the wedge 180. As can be seen, the top side 186 contains an opening 202. The opening 202 (also known as the fenestration) is for application of bone grafting, as well as for locking purposes since the bone would sink into the opening 202.

Figure 17B:
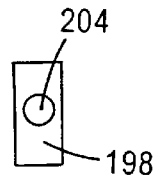
FIG. 17B is an illustration of one side of the wedge seen in FIG. 16.

FIG. 17B depicts the first end 198 of the wedge 180. The first end 198 will have contained thereon a threaded aperture 204. In the preferred embodiment, the first end 198 would be directed posterior in the patient or towards the back of the patient. The threaded aperture 204 is necessary for the application of the inserter means for inserting the device into the intra-vertebral space.

Figure 17D:
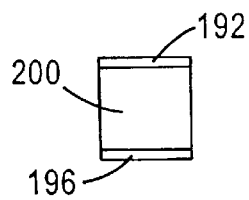
FIG. 17D is an illustration of the second end of the wedge seen in FIG. 16.
Figure 17C:
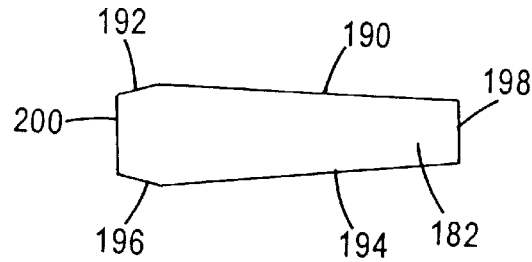
FIG. 17C is an illustration of the lateral view of the wedge seen in FIG. 16.

In FIG. 17C, the first side 182 is shown. This view depicts the angled surfaces 190 and 194 increasing the width of the device until the angled surfaces 192 and 196 are intersected thereby creating a tapered end which leads to second end 200. The point at which the sides 190, 192, 194 and 196 intersect represent the greatest thickness of wedge 180.

FIG. 17D is the second end 200 of the wedge. As seen, the angled surfaces 192 and 196 causes a tapered effect of the wedge at the second end 200. In FIG. 17E, a cross-sectional view taken along line 17E—17E of FIG. 16 is illustrated. Thus, the first end 198 contains the threaded aperture 204, while the wedge 180 contains the opening 202. The second end is represented at 202.

Figure 18:
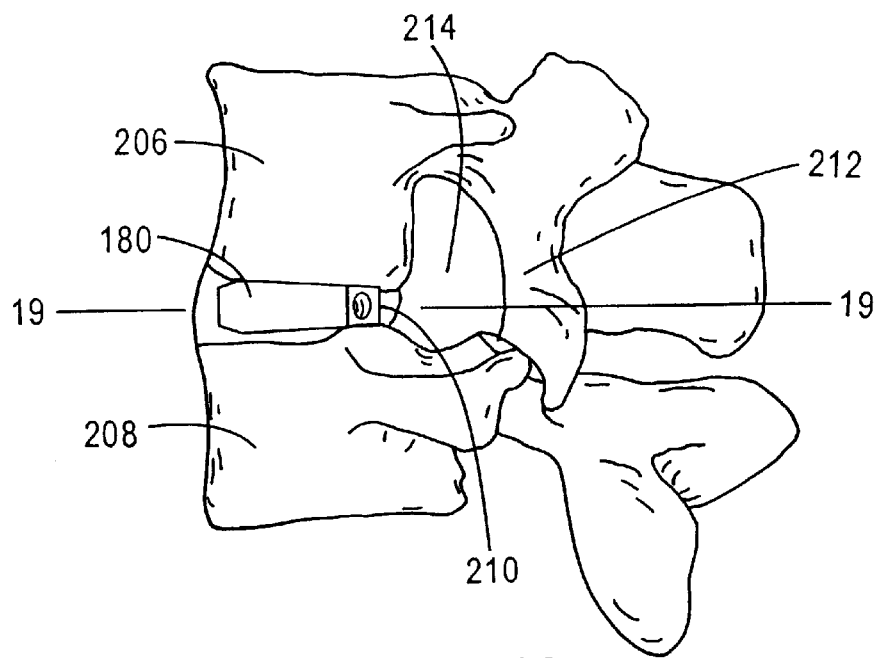
FIG. 18 is a three dimensional illustration of the spinal column depicting two vertebra.

Turning now to FIG. 18, a three dimensional view of the spinal column depicting two vertebra is illustrated. The FIG. 18 depicts the position of the intra-vertebral wedge 180 in position in the spinal column. The wedge 180 is in place between a first anterior vertebral body 206 and a second anterior vertebral body 208. Also depicted is the posterior longitudinal ligament and annulus fibrosis 210, the pars intra-articularis, part of the lamina, which is a bone extending from one vertebra and connects one vertebrae bone to the next 212, and the intra-vertebral foramen 214 which is the hole between each segment of the spine or vertebra that allows for the passage of the nerve roots and the presence of arteries, veins, and fat.

Figure 19:
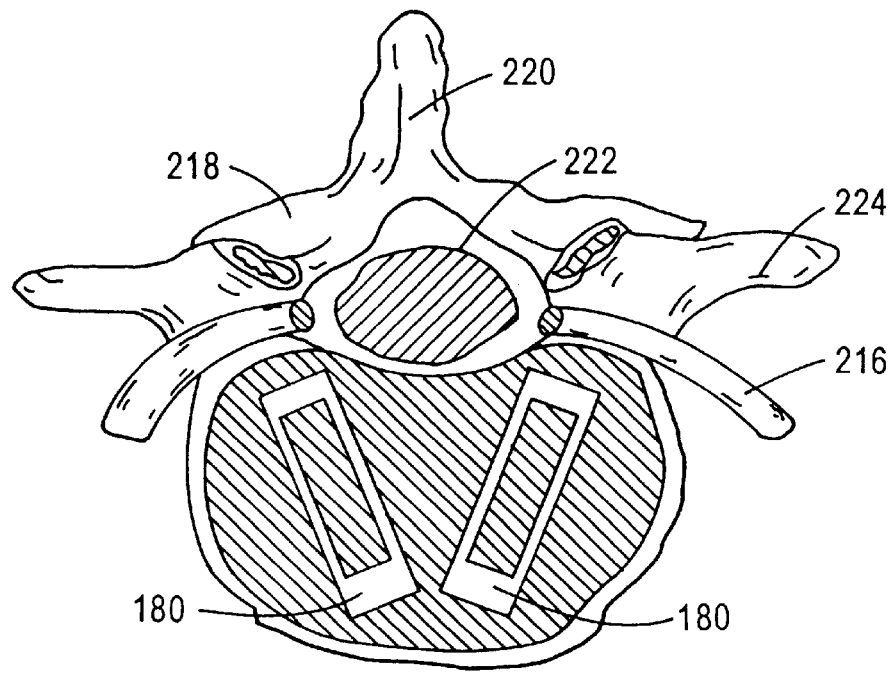
FIG. 19 a cross sectional view through the spinal column taken along line 19—19 of FIG. 18.

In FIG. 19, a horizontal view through the spinal column at the level of the intra-vertebral disc, generally at line 19—19 of FIG. 18, is shown. The purpose is to show the position of the wedges 180 (as seen here, two wedges have been employed) in the disc in a horizontal view of the intra-vertebral view. The wedges 180 converge anteriorly, but do not touch one another. The wedges 180 diverge posterior so that the wedges 180 can be inserted lateral to the nerve roots 216.

The lamina 218, the spinous process 220 which projects posterior of the vertebral column, the spinal cord 222, the transverse process 224, and the nerve root 216 passing out through the intra-vertebral foramen and it progresses anteriorly and inferiorly in front from the spinal column.

Figure 20:
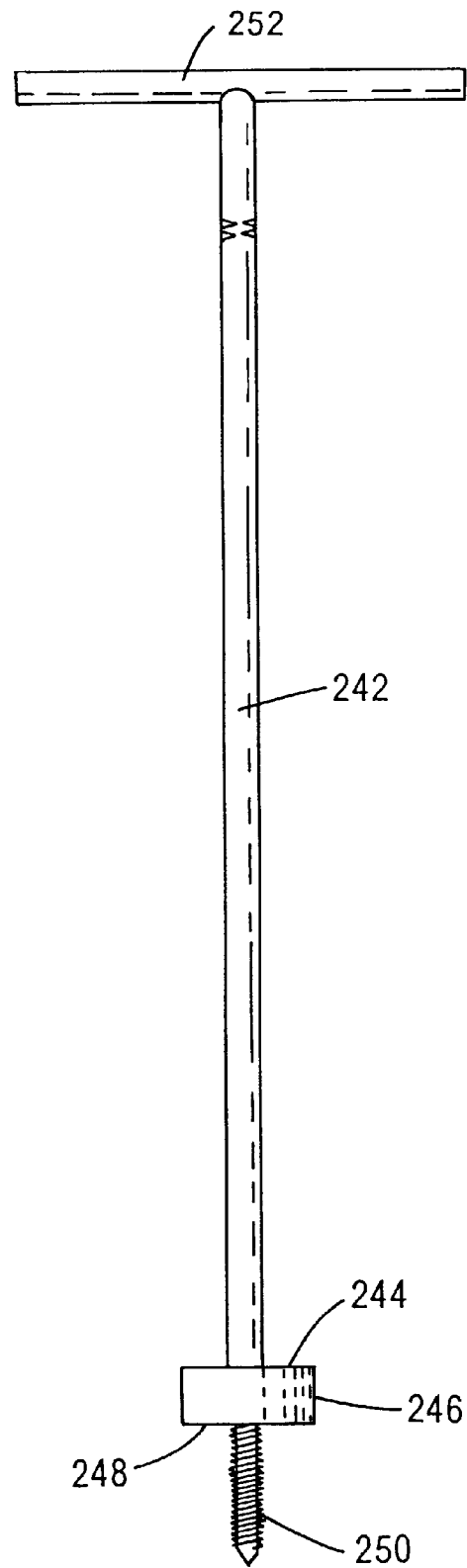
FIG. 20 is an illustration of the wedge inserter device.

Referring to FIG. 20, wedge inserter 240 is shown. The inserter 240 has a generally cylindrical surface 242 that terminates at the radial collar surface 244, with the surface 244 extending to second cylindrical surface 246 that in turn will terminate at radial collar surface 248. The collar surface will have attached thereto the external thread means 250; the thread means 250 will mate and cooperate with the threaded aperture 204. The inserter 240 also has handle means 252 that extends from the cylindrical surface 242.

Figure 21C:
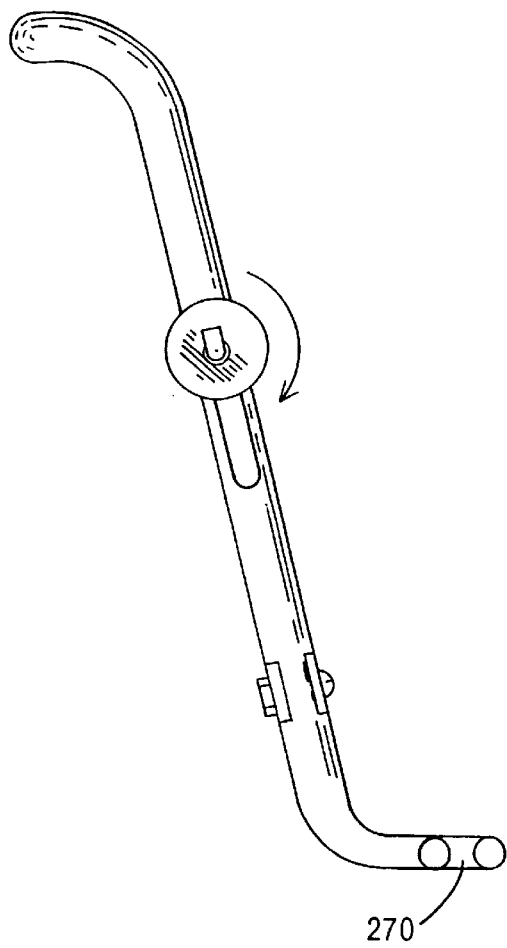
FIGS. 21A, 21B, and 21C illustrate the spreader device.
Figure 21A:
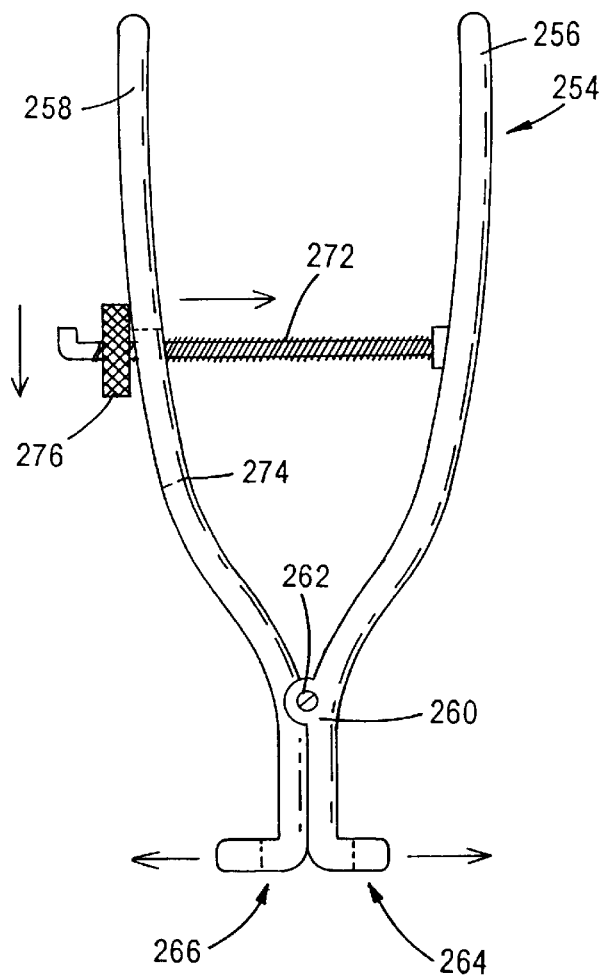
Figure 21B:
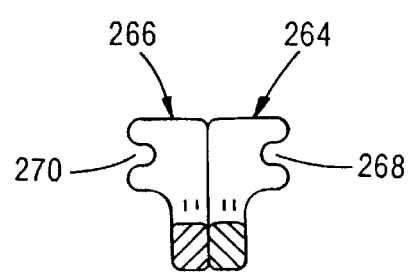

The spreader device 254 is shown in FIGS. 21A, 21B and 21C. The spreader device has a first prong 256 and second prong 258, with prongs 256 and 258 having generally curved surfaces that extend to aperture 260 that has fitted therein a connector pin 262. The prongs will have at one end jaw means 264 and 266, respectively, as seen in FIG. 21B. The jaw means will contain a notched groove 268 and 270 that will be sized so that the notched grooves 268 and 270 fit and cooperate with the stem 46 of the screw 36.

As seen in FIG. 21A, the spreader device has a threaded separating screw 272 that will have contained thereon an external thread. The separating screw 272 fits through a slotted opening 274 in the prong 256. A fastening nut 276 will be provided so that when the spreader device 254 is in use, the nut keeps a constant force applied to the jaw means 264 and 266. Thus, when the correct amount of spreading force has been applied, the fastening nut can be applied in order to fix the jaw means 266, 264 in a static position. Also, as seen in FIG. 21C, a lateral view of the prong 256 depicts the jaw means 264 along with pin 262 and the opening 274 for placement of the separating screw 272.

Figure 22C:
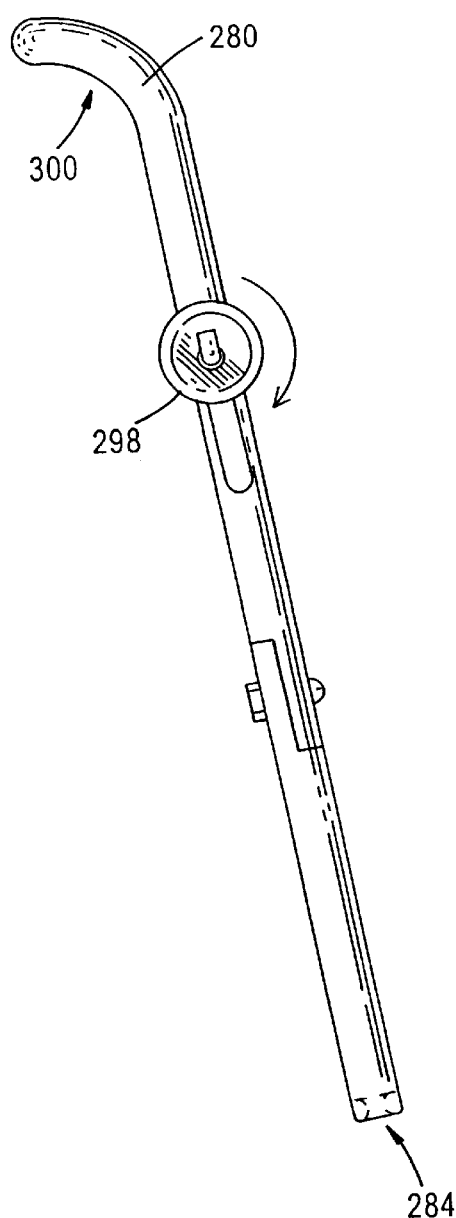
Figure 22A:
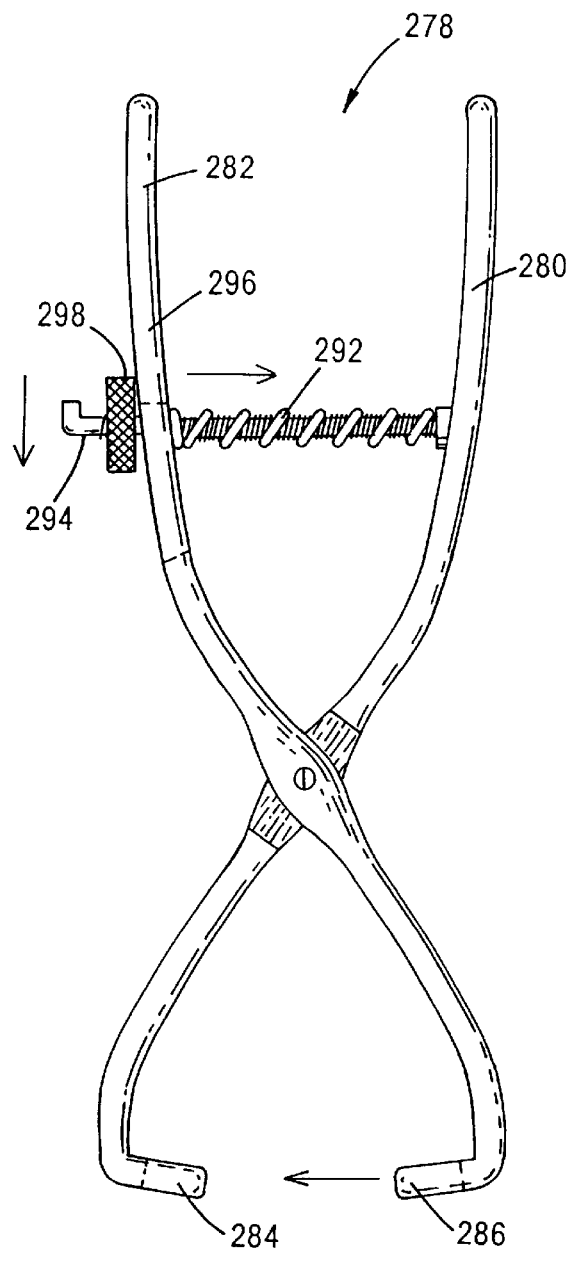
Figure 22B:
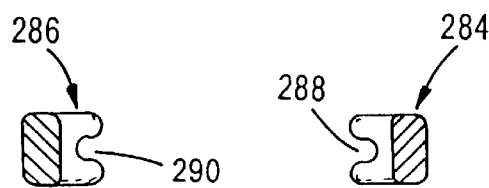

In FIG. 22A, a compressor device 278 is depicted. The compressor device 278 will contain a first prong 280 and a second prong 282 that will contain jaw means 284 and 286, with the jaw means 284 and 286 containing notched grooves 288 and 290, respectively, (as seen in FIG. 22B) that will engage and cooperate with the stem 46 of the screw 36 in a manner similar to the spreader device 254, except jaw means 284 and 286 will apply a compressive force relative to two implanted screws 36. The compressor device 278 will contain a torsion spring 292 that will have fitted therein a stem 294 that will be attached to the prong 280, and the stem will be fitted through the slotted opening 296. A fastening nut 298 will be provided such that the surgeon may set the desired force that jaw means 284 and 286 will be urged together by the torsion spring 292. FIG. 22C shows the lateral view of prong 280 which depicts the curved end 300 as well as the jaw means 284.

Operation

The surgical procedure is done bilaterally through two posterior lateral incisions or one posterior incision, exposure is carried out to the transverse process (FIG. 19, 224) of the spinal diseased segments. Gentle dissection between and lateral to the transverse process exposing the nerve roots (FIG. 19, 216) and the annulus fibrosis (FIG. 18, 210) is carried out in order to expose and visualize the nerve root, disc, vessels and intervertebral foramen.

(The intervertebral foramen is enlarged, if necessary (FIG. 18, 214) by cutting away bone of the superior facet of the lower vertebra increasing the space and soft tissue around the nerve roots.) A small cruciate incision is made in the annulus fibrosis (FIG. 18, 210) posterior laterally near the intervertebral foramen. The gelatinous disc material and cartilage end plate is removed (discectomy) to the vertebral bodies with a pituitary rongeur and a bone burr. This procedure is performed bilaterally down to firm bone but does not cut through the surface of the vertebral body.

At this point in the procedure the intra-pedicle screws are placed in posteriorly for posterior stabilization. The pedicle screws are applied under image intensifier control. The drill point is placed into the vertebral body through the pedicle starting at the base of the transverse process. Transverse processes are the bony extensions projections projecting outward from the side of a vertebrae. There are two transverse processes on each vertebrae, one on each side. The proper size and length of the intra-pedicle screws are then determined.

Next, the pedicle screw is rotated into the bared opening with the wrench. The pedicle screws are placed in the lumbar vertebral bodies bilaterally which needed fixation, which generally is either the pedicle of the fourth, fifth or first sacral vertebra. Two to four screws are placed into the sacrum at the discretion of the surgeon. A spreader is applied to the intra-pedicle screws and the disc is opened to the limits of strong annulus fibrous. 14. The wedge 180 is pre-measured for length, height, and angle of the wedge. Small pieces of bone are taken elsewhere from the patient and are placed into inter-discal space prior to insertion of the wedge 180. Small pieces of bone are also placed in the fenestration of the wedge for intervertebral fusion.

The pre-measured wedge 180 (FIGS. 16 and 17A–E) is inserted bilaterally as seen in FIGS. 18 and 19. As noted earlier, a temporary wedge may be placed within the discal space in order to aid in determining the exact size needed.

The distraction (spreader) on the intra-pedicle screws is released and the elasticity of the annulus fibrosis and adjacent tissue lock the wedge in solidly. The angled shape of the wedge 180 prevents retropulsion which is dangerous to the neural elements. Anterior extrusion of the wedge is prevented by the annulus fibrosis, anterior longitudinal ligament and the locking effect of the compression on the fenestrated wedge.

After the intra-pedicle screws are in place, the position is checked with the image intensifier and a direct visual check. Next, the ball clamp is placed about the spherical handles of the pedicle screw. The fastening member (nut) is tightened so that the ball clamp will not slip off the ball of the pedicle screw.

The particular structure arrangement will vary on a case-by-case basis. Thus, the figures of this application show one possible sequence; however, other arrangements will depend on the particular circumstances so that the connections and cross connections can be many different arrangements.

Once the plan is decided upon, the stabilizing rods, with or without spherical balls on the end, are cut to the proper length. Next, the rods are slipped into the clamps. Then, the compressor device 278 is applied to the intra-pedicle screws of two adjacent vertebra, and the screws are thereafter compressed with device 278. Next, the nuts of the clamping devices are tightened. At this point, completion of the application of the posterior intra-pedicle spinal fixation device is completed.

Figure 23:
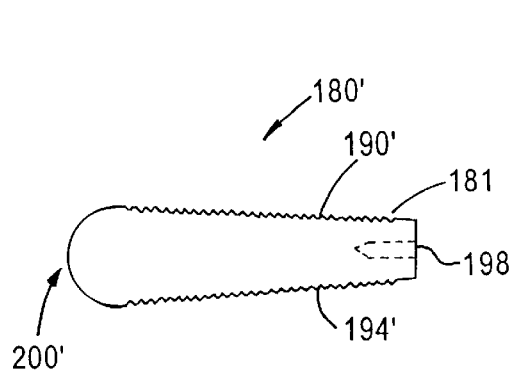
FIG. 23 is an illustration of an alternative wedge configuration in side view.

FIG. 23 illustrates an alternative intervertebral wedge 180'. This embodiment differs from that depicted in FIGS. 16 and 17A–E in the rounded end 200', the serrated edges 190' and 194' and the solid body 181.

The rounded end 200' facilitates insertion of the wedge 181 between vertebrae bodies. The serrated edges 190' and 194' are angled forward toward the narrow end 198 to prevent or minimize posterior extrusion of the wedge after insertion.

The wedge 180' is preferably made with a solid body 181 as opposed to the fenestration-containing wedge depicted in FIG. 17E. The solid body 181 accommodates large and/or heavy individuals which may require more structural surface on the wedge for support. The intervertebral wedge 180' can be configured with one of the rounded end 200', the serrated edges 190' and 194', or the solid body 181, or any combination thereof. The rounded edge and the configuration can also be used with a temporary wedge which may be placed within the discal space to aid in determining the exact size of the wedge.

In another aspect of the invention, the intervertebral wedge can be used without a posterior fixation device. In the surgical procedure described above, pedicle screws are used for posterior stabilization. It has been discovered, however, that a posterior fixation is not necessary when the intervertebral wedges are inserted after the vertebrae bodies are subjected to sequential expansion using a temporary wedge or spacer, i.e., a trial.

The alternative surgical procedure follows the same sequence as described in conjunction with FIGS. 18 and 19 up to the removal of the gelatinous disc material and cartilage end plate. Instead of placing the intra-pedicle screws posteriorly for posterior stabilization, a series of sequential expansions of the adjacent vertebral bodies are performed using trials having different sized distal ends.

Figure 24:
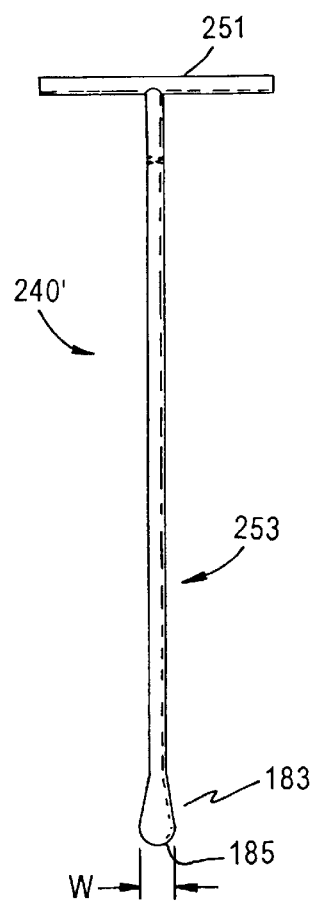
FIG. 24 is an illustration of an alternative wedge inserter device.

FIG. 24 depicts a trial 240' having a handle 251 and a shaft 253. Integrally attached to the distal end of the shaft 253 is the trial end 183. The trial end 183 has a rounded portion 185 which facilitates insertion of the trial end between the adjacent vertebrae bodies.

The trial end has a plate like thickness (not shown in FIG. 24) and a wide end having a width measurement designated by the letter "W". The trial end 183 can be made separate from the shaft 253 so that different sized trial ends 183 could be used with the same handle and shaft combination. This embodiment is similar to the wedge inserter depicted in FIG. 20 for insertion of the wedge implant 180.

Prior to the surgical procedure of stabilizing the motion of a plurality of involved spinal diseased vertebrae with the intervertebral body wedge, a large selection of paired trial spaces is provided with trial ends of increasing widths. For example, the paired trials could range from 6 mm to 16 mm for the dimension "W". Once the gelatinous disc material and cartilage end plate are removed as described above, a trial having a relatively narrow trial end is then placed in either the right of left side of the inter-discal or intervertebral space. Leaving this trial in place, a wider trial is then placed in the other side of the intervertebral space. This sequence of trial insertions is then alternated with trials of increasing width. The trial that has been inserted is removed once a wider trial is inserted in its place. The removal step can be done simultaneously, before or after insertion of the wider trial. The intervertebral disc is open to a maximum height and annulus fibrosis is stretched to its limit. This condition can be sensed by the degree of movement that can be imparted to the trial once it is inserted in the intervertebral space. When the maximum height is reached, the trial is substantially immovable after being inserted. This tells the surgeon that the intervertebral wedges can be implanted.

In order to gain rigid stability between two adjacent vertebra by placing two intervertebral body wedges in the intervertebral disc spaces without using some type of posterior internal fixation device, the wedges should be press fit in place. The press fit is obtained by increasing the intervertebral disc height until the peripheral ligaments and annulus fibrosis are stretched to the limit. By reaching this maximum limit through the sequential trial insertion steps described above, the intervertebral body wedge implant can be inserted into the intervertebral space as described above. After withdrawal of the trial after wedge insertion, the elasticity of the annulus fibrosis and adjacent tissue lock the wedge in solidly. The other intervertebral body wedge can then be implanted and its associated trial removed for stabilization of the spinally diseased vertebrae. By expanding the inter-discal space to its maximum using the sequential insertion of the trials, the intervertebral body wedges are press fit and no posterior fixation device is required.

In the surgical procedure described using the intra-pedicle screws, the intervertebral foramen is enlarged by cutting away bone of the superior facet of the lower vertebrae, thereby increasing the space and soft tissue around the nerve roots. When implanting the intervertebral body wedges without the posterior fixation devices, it has been discovered that additional bone excision can be performed to provide improved visualization and entry into the intervertebral disc without touching or retracting the spinal cord or nerve root. This additional bone excision is adaptable for both of the surgical procedures of the invention.

Figure 25:
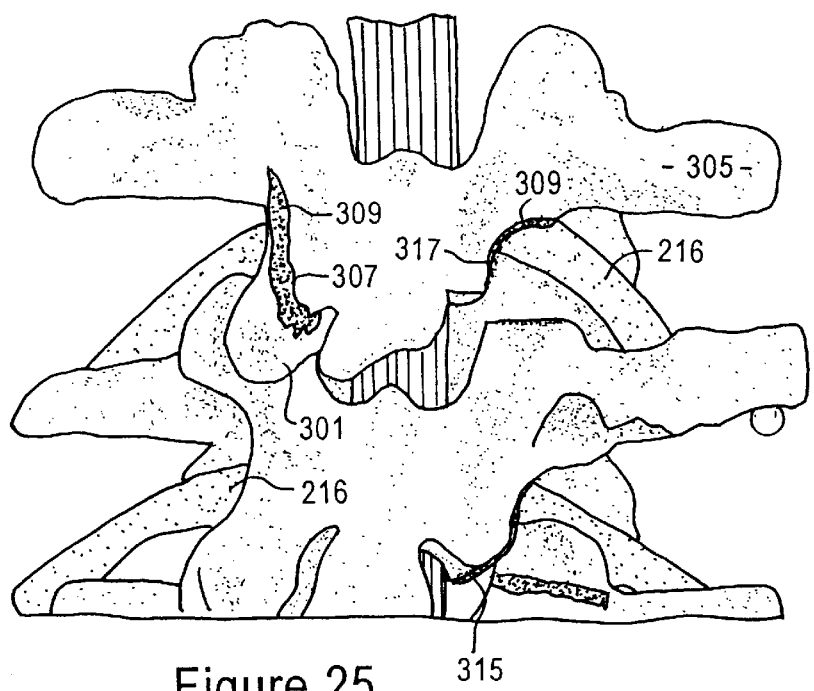
FIG. 25 is a photographic illustration showing bone excision as part of the surgical procedure using only the intervertebral body wedge.

Referring to FIG. 25, a photographic posterior view of a nodel of a spinal column section is designated by the reference numeral 300. This view more clearly shows the areas of bone excision to facilitate implanting the wedges. First, the entire inferior facet 301 of the cephalad vertebrae 305 is removed as well as some of the pars-inter-articularis 307. The extent of removal is shown by the marking 309.

A part of the superior facet of the caudad vertebrae is removed. One superior facet is identified by reference numeral 311 on the vertebrae beneath the vertebrae 313. The extent of removal is indicated by the line marking 315. The superior facet is removed superiorly and central to the pedicle. Excision of the inferior and superior facets leaves a gap 317 which allows excellent visualization and entry into the intervertebral disc without touching or retracting the spinal cord 222 or nerve root 216.

As part of the surgical procedure, the size of the intervertebral body wedge can be estimated using X-ray techniques and a known-dimensioned article such as a ball. The pre-measured ball is placed over the vertebral spinous process of the lower lumber vertebra. A lateral X-ray film is then taken. The magnification or reduction is calculated by measuring the ball on the X-ray. The actual diameter of the ball divided by the measurement on the X-ray equals a percentage of the magnification or reduction. Then, lines are drawn on the base plate on each side of the intervertebral disc as shown on the X-ray. These lines define the angle of the wedge.

The disc height is measured 1 cm posterior to the anterior edge of the vertebrae and ½ cm anterior to the posterior edge of the vertebrae. The normal intervertebral disc adjacent is also measured. The height of the normal disc is then used to estimate the size of the implant taking into account the magnification and reduction percentage calculated above. With this estimate, various sized intervertebral body wedges can be made so that a precise fit can be obtained by selecting the right sized wedge.

Using only the intervertebral wedges without the posterior fixation device provides significant advantages in terms of the surgical procedure and the patient. First, rigid anterior stabilization is achieved from the posterior.

Second, a posterior lateral approach permits the excision of the facet joint, does not expose the dura or nerve roots and permits the pedicle to remain connected to the lamina and spinous process. The excision of the facet joint also enlarges the vertebral foramen. By not exposing the dura or nerve roots, less scar tissue forms and the diskectomy is simplified. By leaving the pedicle connected to the lamina and the spinous process, a large posterior bone bed remains for grafting and the spinal cord remains protected by the lamina.

Use of the intervertebral body wedge also restores normal disc height and permits use of the subchondral bone for support of the wedge. By using the subchondral bone, less bleeding and less sinking of the device into the vertebral body occurs. Restoring the normal disc height enlarges the intervertebral foramen and also retracts bulging annular fibrosis.

Using the various sized trials, the correct length, height and angle of the intervertebral body wedge can be readily determined. The use of the intervertebral body wedge alone restores lumbar lordosis, i.e., decreases tension on nerve roots and eliminates the distraction required when using the intra-pedicle screws. The wedge shape of the intervertebral body device also restores lumbar lordosis and minimizes posterior expulsion. Using the serrated edges on the wedge shape enhances the wedge fixation and further reduces the possibility of posterior expulsion.

The surgical procedures described above relating to intervertebral fusion can also be practiced with the alternative surgical procedure using just the body wedge.

Although a pair of intervertebral body wedges are disclosed for implantation, one or more than two could be implanted depending on the patient and extent of spinal disease. In addition, other techniques may be used to estimate the size of the intervertebral body wedge rather than the X-ray technique described above. For example, wedge sizes could be based on the sizes of wedges implanted in previous surgeries or the manufacture of a number of wedges which vary incrementally in width, thickness and angulation.

Changes and modifications in the specifically described embodiments can be carried out without departing from the scope of the invention which is intended to be limited only by the scope of the appended claims.

I claim:

1. A method of stabilizing motion of a plurality of involved spinal diseased vertebrae with a spinal fixation device, the spinal fixation device containing a plurality of pedicle screws, the pedicle screws containing a first and second end, the first end containing thread means and the second end containing a spherical handle end and a multi-sided fastening member, the spinal fixation device further containing a plurality of ball clamp means for securing onto the spherical handle ends, a plurality of interconnecting rods for interconnecting the ball clamp means, and a wedge member, the method comprising the steps of:
  a. performing two posterior lateral incisions or one posterior incision on a back of a patient to an area of the involved spinal diseased vertebrae;
  b. exposing a transverse process of the involved spinal diseased vertebrae;
  c. dissecting between and lateral to the transverse process of the involved spinal diseased vertebrae so that nerve roots and an annulus fibrosis are exposed;
  d. placing a cruciate incision in the annulus fibrosis posterior laterally near an intervertebral foramen;
  e. removing a gelatinous disc material and cartilage end plate of the involved spinal diseased vertebrae to form an inter-discal space;
  f. determining a proper size and length of the pedicle screws;
  g. placing a drill point on a vertebral body starting at the base of the transverse process of each of the involved spinal diseased vertebrae;
  h. drilling bore holes in the pedicles of the involved spinal diseased vertebrae for placement of the pedicle screws;
  i. rotating the pedicle screws into the bored holes of the involved spinal diseased vertebrae; and
  j. applying a spreader to the pedicle screws to expand the inter-discal space to receive the wedge member.

2. The method of claim 1, further comprising the steps of:
  k. selecting a proper length, height, and angle of the wedge member;
  l. placing a bone in small pieces into the inter-discal space of the involved spinal diseased vertebrae, and in a fenestration of the wedge for intervertabral fusion;
  m. inserting the wedge into the inter discal space of the involved spinal diseased vertebrae bilaterally;
  n. releasing the spreader from the pedicle screws which had been keeping the involved spinal diseased vertebrae separated so that the elasticity of the annulus fibrosis and adjacent tissue lock the wedge between the involved spinal diseased vertebrae.

3. The method of claim 2 further comprising the steps of:
  o. examining the position of the pedicle screws with an image intensifier;
  p. placing the ball clamp means about the spherical handles of the pedicle screws;
  q. tightening the fastening member so that the ball clamp means will not slip of the spherical handle of the pedicle screw;
  r. determining a particular structure arrangement of the interconnecting stabilizing rods;
  s. cutting the interconnecting stabilizing rods, with or without spherical balls on the end, to a proper length;
  t. placing the interconnecting rods into the ball clamp means so that the ball clamp means are linked; and
  u. tightening the ball clamp means so that the ball clamp means envelopes the spherical handle end and the interconnecting rods.

4. The method of claim 3 wherein the step of placing the drill points on the involved spinal diseased vertebral bodies and drilling the bore holes in the involved spinal diseased vertebral bodies includes:
  v. placing the drill point on a first and second site of a pedicle of a sacrum;
  w. placing the drill point on a first and second site of an ala of the sacrum and drilling a bore hole to the first and second site on the ala of the sacrum;
  x. placing the drill point on a first and second site of a pedicle of an L5 involved spinal diseased vertebral body and drilling a bore hole to the first and second site of the L5 involved spinal diseased vertebral body; and
  y. placing the drill point on a first and second site of a pedicle of a second involved spinal diseased vertebral body and drilling a bore hole to the first and second site of an L4 involved spinal diseased vertebral body.

5. A method of stabilizing a motion of a plurality off involved spinal diseased vertebrae with an intervertebral body wedge comprising the steps of:
  a. performing two posterior lateral incisions or one posterior incision on a back of a patient to an area of the involved spinal diseased vertebrae;
  b. exposing a transverse process of the involved spinal diseased vertebrae;
  c. dissecting between and lateral to the transverse process of the involved spinal diseased vertebrae so that nerve roots and the an annulus fibrosis are exposed;
  d. placing a cruciate incision in the annulus fibrosis posterior laterally near an intervertebral foramen;
  e. removing a gelatinous disc material and cartilage end plate of the involved spinal diseased vertebrae to form an inter-discal space;
  f. expanding the inter-discal space by inserting a first spacer between adjacent vertebral bodies at a first site, further expanding the inter-discal space by inserting a second spacer between adjacent vertebral bodies at a second site;
  g. repeating step (f) using spacers of increasing width until a maximum inter-discal spacing is reached;

h. inserting at least one intervertebral body wedge at one of the first site and the second site and removing said respective spacer so that the intervertebral body wedge is press fit between the adjacent vertebral bodies.

6. The method of claim 5, wherein an intervertebral wedge is inserted at each of the first and second sites.

7. The method of claim 5, wherein a size of the intervertebral wedge is estimated by the steps of:
   i) prior to step (a), placing a pre-measured ball over a vertebral spinous process of a vertebra located in a region to be stabilized;
   ii) taking an X-ray of the pre-measured ball and the vertebra and calculating a magnification or reduction of the X-ray based on a dimension of the ball on the X-ray;
   iii) determining an angle of an intervertebral disk based on the X-ray;
   iv) determining an inter-discal spacing based on said magnification or reduction and the X-ray; and
   v) sizing the intervertebral wedge based on the angle and the inter-discal spacing.

8. The method of claim 5, further comprising the steps of: prior to step (d), removing an entire inferior facet of a cephalad vertebra, a portion of the pars-inter-articularis of the cephalad vertebra and a portion of a superior facet of the caudad vertebra, the portion of the superior facet removed superiorly and central to the pedicle.

9. The method according to claim 5, comprising the step of placing a bone in small pieces into the inter-discal space of the involved spinal diseased vertebrae for intervertebral fusion.

10. The method according to claim 9, comprising providing an intervertebral wedge with a fenestration and placing the small pieces in the fenestration for the intervertebral fusion.

11. The method according to claim 5, wherein the intervertebral wedge comprises:
   i) a wedge body having a distal leading end and a proximal end opposing side faces and opposing side edges, the body opposing sides tapering in width from the distal leading end to the proximal end.

12. The method according to claim 9, wherein the distal leading end is rounded.

13. The method according to claim 9, wherein the side edges have serrations, the serrations angled toward the proximal end.

14. The method according to claim 9, wherein the wedge body has a fenestration.

15. The method according to claim 5, wherein each spacer is mounted to a spacer insertion tool.

16. The method according to claim 5, wherein each spacer is tapered in shape from a wider distal leading end to a more narrow proximal end.

17. The method of according to claim 5, wherein the sequential repeating step further comprises:
   i) removing the first spacer and inserting a wider spacer, then removing the second spacer and inserting a spacer wider then the second spacer; and
   ii) continuing the removing and inserting steps of i) using progressively wider spacers until the maximum inter-discal spacing is reached.

* * * * *